United States Patent
Toyoda et al.

Patent Number: 6,120,486
Date of Patent: Sep. 19, 2000

[54] DISPOSABLE DIAPER WITH THREE DIMENSIONAL GATHERS

[75] Inventors: Harumitsu Toyoda; Haruko Toyoshima; Jun Sasaki, all of Tochigi, Japan

[73] Assignee: Kao Corporation, Tokyo, Japan

[21] Appl. No.: 08/849,611

[22] PCT Filed: Sep. 24, 1996

[86] PCT No.: PCT/JP96/02746
§ 371 Date: Jun. 4, 1997
§ 102(e) Date: Jun. 4, 1997

[87] PCT Pub. No.: WO97/12571
PCT Pub. Date: Apr. 10, 1997

[30] Foreign Application Priority Data

Oct. 5, 1995 [JP] Japan ................... 7-259069
Oct. 31, 1995 [JP] Japan ................... 7-283185

[51] Int. Cl.[7] ............................................. A61F 13/15
[52] U.S. Cl. ................................. 604/385.2; 604/385.1
[58] Field of Search .................... 604/385.1, 385.2, 604/386, 391

[56] References Cited

U.S. PATENT DOCUMENTS

| | | | |
|---|---|---|---|
| 4,743,246 | 5/1988 | Lawson | 604/385 A |
| 4,795,454 | 1/1989 | Dragoo | 604/385.2 |
| 4,850,990 | 7/1989 | Huntoon et al. | 604/385.2 |
| 4,938,755 | 7/1990 | Foreman | 604/385.2 |
| 5,021,051 | 6/1991 | Hiuke | 604/385.2 |
| 5,026,364 | 6/1991 | Robertson | 604/385.2 |
| 5,167,653 | 12/1992 | Igaue et al. | 604/385.2 |
| 5,246,432 | 9/1993 | Suzuki | 604/385.2 |
| 5,292,316 | 3/1994 | Suzuki | 604/385.2 |
| 5,304,159 | 4/1994 | Tanji et al. | 604/385.2 |
| 5,558,660 | 9/1996 | Dreier | 604/385.2 |
| 5,569,234 | 10/1996 | Buell et al. | 604/385.2 |
| 5,746,732 | 5/1998 | Olsson et al. | 604/385.2 |
| 5,776,121 | 7/1998 | Roe et al. | 604/385.1 |

FOREIGN PATENT DOCUMENTS

| | | | |
|---|---|---|---|
| 412579 | 2/1991 | European Pat. Off. | |
| 437771 | 7/1991 | European Pat. Off. | |
| 567105 | 10/1993 | European Pat. Off. | |
| 2 699 813 | 7/1994 | France | 604/385.2 |
| 2 701 207 | 8/1994 | France | 604/385.2 |
| 2 241 871 | 9/1991 | United Kingdom | 604/385.2 |
| 2259441 | 3/1993 | United Kingdom | |
| 2287393 | 9/1995 | United Kingdom | |
| 93/09739 | 5/1993 | WIPO | 604/385.2 |
| 9410952 | 5/1994 | WIPO | |
| 9428844 | 12/1994 | WIPO | |

*Primary Examiner*—Mark O. Polutta

[57] ABSTRACT

A disposable diaper according to the present invention includes a liquid permeable top sheet, a liquid impermeable back sheet, and a liquid retentive absorbent member interposed between the top sheet and the back sheet, and having a pair of inner sheets which are connected to the back sheet and are provided at opposite longitudinal side portions of the disposable diaper on its top sheet side such that the longitudinal inner side edges of the inner sheets are located inwardly along the longitudinal side edges of the absorbent member. Each of the inner sheets includes a laminate of a non-woven fabric and a film, and each inner sheet is arranged such that the non-woven fabric is located on the skin-contacting surface side of the diaper, and wherein the back sheet includes a laminate of non-woven fabric and a film. The back sheet is arranged such that the non-woven fabric is located on the outer skin-noncontacting surface side of the laminate.

12 Claims, 9 Drawing Sheets

DISPOSABLE DIAPER WITH THREE DIMENSIONAL GATHERS

TECHNICAL FIELD this application is the national phase under 35 U.S.C. §371 of prior PCT International Application No. PCT/JP96/02746 which has an International filing date of Sep. 24, 1996 which designated the U.S.A.

This invention relates to a disposable diaper, and more particularly to a disposable diaper having a liquid absorbing surface over the entire surface of the diaper which comes into contact with the skin of the diaper wearer.

BACKGROUND OF THE INVENTION

For infant disposable diapers, many types of anti-leakage mechanisms have heretofore been proposed for the purposes of preventing leakage of liquid from the leg portions. In one example, hydrophobic three-dimensional gathers are formed on an inner side of each leg gather in the longitudinal direction of the diaper, and the three-dimensional gathers are collapsed inwardly. The three-dimensional gathers tend to be raised to some extent when the diaper is in use, and serve as antileakage portions owing to their hydrophobic properties, thereby enhancing the receiving characteristics of discharged material and preventing liquid leakage from the leg portions, which would otherwise occur in accordance with the motion of the diaper wearer.

Further, in the above-mentioned three-dimensional gathers, it is true that the receiving characteristics of the diaper for discharged material are enhanced due to so-called pocket portions which are formed by the three-dimensional gathers. However, there are many instances where the three-dimensional gathers collapse under e.g. body pressure of the diaper wearer when the diaper is in use, and therefore the advantageous effects attributable to the three-dimensional gathers can not be fully exhibited. Furthermore, depending on the motion of the diaper wearer, liquid diffuses in various directions within the diaper and frequently leaks outside the three-dimensional gathers. In such cases, the outside area of the three-dimensional gathers is hydrophobic and no absorbent member is provided. Accordingly, the liquid which has leaked is allowed to flow directly outside the disposable diaper without being absorbed. Moreover, since the leg gathers themselves are not three-dimensional, the leg gathers do not have such an anti-leakage function, as the above-mentioned three-dimensional gathers, and the leg gathers cannot prevent liquid from leaking.

As means for solving such problems, there can be contemplated, among others, that the expanding/contracting force of the elastically expansible members disposed on the free edge portions of the three-dimensional gathers is increased. However, any attempt for merely increasing the expanding/contracting force is encountered with disadvantages such as the diaper is contracted in size and badly irritates the skin of the diaper wearer.

Further, in the above-mentioned three-dimensional gathers, there are many instances where discharged material is locally absorbed. As a result, in spite of the feature that the absorbent member is arranged over the entire surface of the diaper, it is only a part of the absorbent member that actually contributes to absorption of the discharged material and therefore, the inherent absorbing performance of the absorbent member can not be fully realized in many cases. Furthermore, due to local absorption of the discharged material, particularly due to local absorption of the discharged material at the discharging area and its adjacent areas (i.e., the crotch portion of the diaper), it sometimes occurs that the diaper slips down or sags to degrade the fit. The result is that the discharged material tends to leak and the diaper wearer finds it difficult to move. Moreover, in some instances, the diaper is partly expanded (puffed out), which spoils its outer appearance.

It is, therefore, an object of the present invention to provide a disposable diaper, in which liquid can assuredly be absorbed and prevented from leaking when the liquid tends to disperse in various directions in accordance with motion of the diaper wearer.

Another object of the present invention is to provide a disposable diaper, in which the inherent absorbing performance of an absorbent member can fully be exhibited by preventing local absorption of the discharged material, and unfavorable occurrences such as slip-down, leaking, bagginess, and the like, do not happen even by the weight of the discharged material.

DISCLOSURE OF THE INVENTION

As a result of hard study, the inventors found that the above objects can be achieved by a disposable diaper capable of absorbing discharged material through its entire surface.

They also found that the above objects can be achieved by providing a disposable diaper in which the leg gathers and three-dimensional gathers are formed into a unitary body so that a three-dimensional round-shaped leg portion is obtained.

The present invention is accomplished based on the above finding, and achieves the above objects by providing a disposable diaper comprising a liquid permeable topsheet, a liquid impermeable backsheet, and a liquid retentive absorbent member interposed between the topsheet and the backsheet, and having a pair of inner sheets which are connected to the backsheet and are provided at opposite longitudinal side portions of the disposable diaper on its topsheet side such that longitudinal inner side edges of the inner sheets are located inwardly along the longitudinal side edges of the absorbent member, each of the inner sheets comprises a laminate of a non-woven fabric and a film, and is arranged such that the non-woven fabric is located on the skin-contacting surface side of the diaper, and wherein the backsheet comprises a laminate of a non-woven fabric and a film, and is arranged such that the non-woven fabric is located on the outer skin-noncontacting surface side of the laminate (Hereinafter, the "first aspect of the invention").

The present invention also provides a disposable diaper comprising a liquid permeable topsheet, a liquid impermeable backsheet, and a liquid retentive absorbent member interposed between the topsheet and the backsheet, and having a pair of inner sheets which are connected to the backsheet and are provided at opposite longitudinal side portions of the disposable diaper on its topsheet side such that longitudinal inner side edges of the inner sheets are located inwardly along the longitudinal side edges of the absorbent member, first elastically expansible members provided at connecting portions which are located between the backsheet and each of the inner sheets to form leg gathers, and second elastically expansible members provided at each of the inner side edges of each of the inner sheets to form frill portion gathers, the topsheet and the inner sheets being jointed together between the longitudinal side edges of the absorbent member and the inner side edges of the inner sheets to form frill portions such that the frill portion gathers define free edges, and wherein approximate center portions of the frill portion gathers along the longitudinal direction thereof and inner portions located inwardly from the approximate centers of the leg gathers along the longitudinal direction thereof are joined together such that the frill portions and the leg gathers are raised (Hereinafter, the "second aspect of the invention").

The present invention further provides a disposable diaper comprising a liquid permeable topsheet, a liquid impermeable backsheet, and a liquid retentive absorbent member interposed between the topsheet and the backsheet, and having a pair of liquid impermeable folded-back sheets which are connected to the backsheet and are provided at opposite longitudinal side portions of the disposable diaper on its topsheet side, and an area on the topsheet side other than the folded-back sheets which serves as a liquid absorbing area, and a pair of elastically expansible members provided at least at opposite side edge portions of the diaper to form leg gathers (Hereinafter, "another embodiment" of the invention).

DETAILED DESCRIPTION OF THE INVENTION

Figure 1:
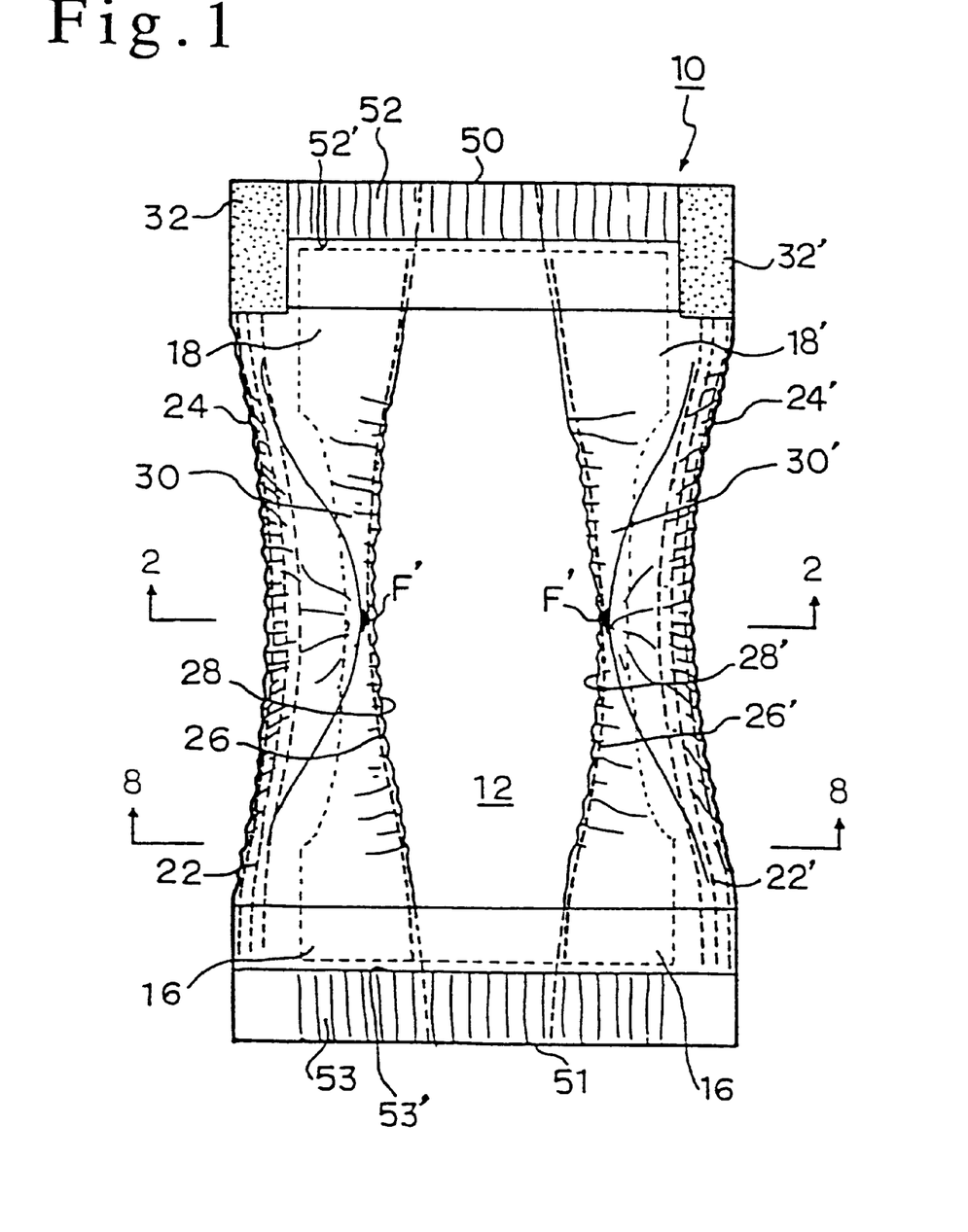
FIG. 1 is a development view showing the first embodiment of a disposable diaper according to the first aspect of the invention.

The preferred embodiments of a disposable diaper according to the first aspect of the invention will be described with reference to the drawings. FIG. 1 is a development view showing the first embodiment of a disposable diaper according to the first aspect of the invention, FIG. 2 is a sectional view taken on line 2—2 of the disposable diaper of FIG. 1 which is in its relaxed state, and FIG. 3 is a perspective view showing the state that a rear waist body portion and a front waist body portion are secured by fixing members.

Figure 2:
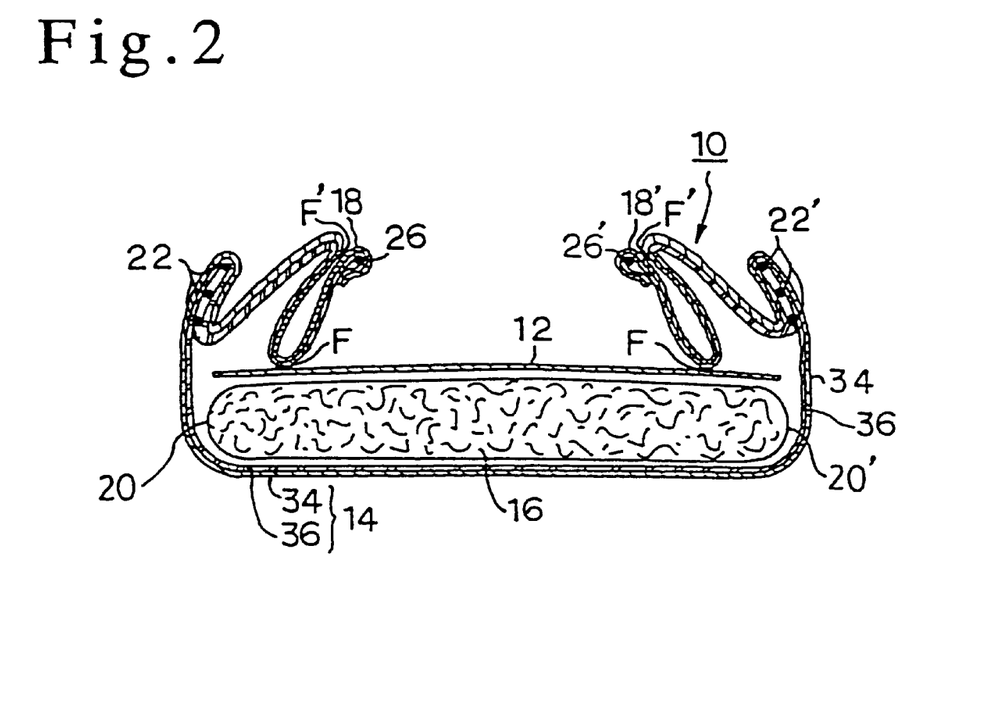
FIG. 2 is a sectional view taken on line 2—2 of the disposable diaper of FIG. 1 which is in its relaxed state.
Figure 3:
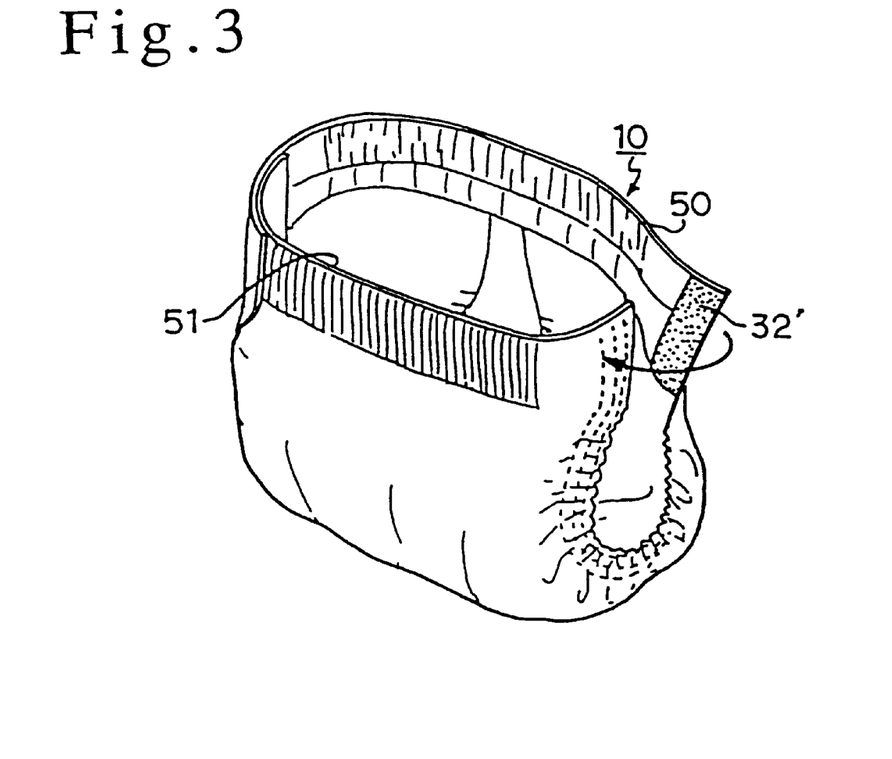
FIG. 3 is a perspective view showing the state that a rear waist body portion and a front waist body portion are secured by fixing members.

A disposable diaper 10 according to the embodiment shown in FIGS. 1 and 2 includes a liquid permeable topsheet 12, a liquid impermeable backsheet 14, and a liquid retentive absorbent member 16 interposed between the topsheet 14 and the backsheet 14.

The liquid permeable topsheet 12 is not particularly limited, and anything can be used as the topsheet 12 as long as it has such properties as being able to permeate discharged material to the absorbent member 16. It is preferable that the topsheet is selected from those which have the feel something like human skin, in particular. Acceptable examples of such liquid permeable sheet include thermoplastic resin woven fabrics, and non-woven fabrics, such as carded or spun-bonded non-woven fabric, and a perforated film. In order to enhance the liquid permeability of the topsheet, a hydrophilic compound, such as alkyl phosphate may be applied to its surface.

As the material for the liquid retentive absorbent member 16, fluff pulp obtained by crushing wood pulp can be used. Preferably, the fluff pulp is used in combination with a superabsorbent polymer. A mixture of thermoplastic resin, fluff pulp and a superabsorbent polymer which has been subjected to heat treatment is still preferred. The superabsorbent polymer may be mixed with the fluff pulp or it may exist in a particular part of the absorbent member 16, namely, an upper part, an intermediate part or a lower part. The superabsorbent polymer preferably has the fixing property capable of fixing a liquid twenty times or more of its dead weight and is in the granular form having the properties readily gelled. Examples of such superabsorbent polymers include proteins, cellulosic materials and synthetic polymers. Among them, a starch-acrylic acid (salt) graft copolymer, a saponified starch-acrylonitrile copolymer, cross-linked sodium carboxymethyl cellulose and acrylic (salt) polymer are still preferred.

In the disposable diaper of FIG. 1, there are provided a rear waist body portion 50 which is located, when in use, on the back side of the diaper wearer and a front waist body portion 51 which is located, when in use, on the stomach side of the diaper wearer. The rear and front waist body portions 50 and 51 are jointed together to form a waist opening portion. In the rear waist body portion 50 and the front waist body portion 51, the topsheet 12, the backsheet 14, and a waist elastically expansible member (not shown) interposed therebetween are jointed together by fixing means such as hot melt or the like, thereby forming rear waist gathers 52 and front waist gathers 53. As the material for the waist elastically expansible member, a yarn-like or strip-shaped polyurethane, natural rubber or the like can be used. Particularly preferably, yarn rubber, flat rubber, film type rubber, film-like foamed urethane, or the like can be used.

In the disposable diaper of this embodiment, as shown in FIGS. 1 and 2, inner sheets 18, and 18' which are connected to the backsheet 14 are provided at opposite longitudinal side portions of the disposable diaper 10 on its topsheet 12 side such that longitudinal inner side edges of the inner sheets 18, 18' are located inwardly of the longitudinal side edges 20, 20' of the absorbent member 16.

More specifically, in the disposable diaper according to this embodiment, as shown in FIGS. 1 and 2, opposite longitudinal side portions of the backsheet 14 are folded back towards the topsheet 12 side, thereby forming the inner sheets 18, and 18' which are connected with the backsheet 14. The inner sheets 18, and 18' are disposed along the entire longitudinal length of the disposable diaper 10. Widths of the inner sheets 18, 18' are approximately the same. In view of the leg, gathers being rounded and three dimensionally raised, the total width of the inner sheets 18, and 18' is preferably 55% or more of the width of the absorbent member 16 when viewing the topsheet side of the flattened state diaper (as shown in FIG. 1) from the direction perpendicular to the topsheet.

As shown in FIG. 2, the inner sheets 18, and 18' are arranged such that their longitudinal inner side edges are located inwardly of the longitudinal side edges 20, 20' of the absorbent member 16. In view of absorption efficiency, the total width of the inner sheets 18, and 18' which lie on the absorbent member 16 is preferably 85% or less of the width of the absorbent member 16 when viewing the topsheet side of the flattened state diaper (as shown in FIG. 1) from the direction perpendicular to the topsheet.

As shown in FIG. 2, each of the inner sheets 18, and 18' comprises a laminate of a non-woven fabric 36 and a liquid impermeable film 34, and is arranged such that the non-woven fabric 36 is located on the skin-contacting surface side of the diaper. The backsheet 14 comprises a laminate of the liquid impermeable film 34 and the non-woven fabric 36, and is arranged such that the non-woven fabric 36 is located on the outer skin-noncontacting surface side of the laminate. The inner sheets arranged on the topsheet 12 side of the diaper are connected with the backsheet as described above. However, the material of the inner sheets may be different from that of the backsheet. As described above, since the outer surface (skin-noncontacting surface) of the disposable diaper according to this embodiment is made of a non-woven fabric, it has the feel something like a cloth and can offer a pleasant feel of use. Further, by using mechanical fasteners, as later described, as fixing members, the fixing members can be secured to any location of the non-woven fabric. Accordingly, the size of the waist portion of the diaper can be adjusted appropriately to match with the body dimensions of the wearer. Moreover, since the fixing members can be attached and detached as often as required, the diaper, which is temporarily removed from the wearer, can easily be put on the wearer. In this embodiment, the non-woven fabric 36 in the backsheet may be laminated over the entire surface of the backsheet, or it may be laminated only on a part of the surface (for example, only the outer surface (skin-noncontacting surface) of the rear waist body portion where the fixing members are to be secured to the backsheet.

The liquid impermeable film 34 is preferably a film sheet obtained by adding an inorganic or organic filler to a thermoplastic resin, a melt extruded from a T-die or circular die, and then monoaxially or biaxially oriented. Moreover, this film sheet is preferably a moisture permeable and liquid impermeable sheet.

As shown in FIGS. 1 and 2, in the disposable diaper according to this embodiment, first elastically expansible members 22, and 22' are, in stretched states thereof, fixedly arranged at a connecting portion (the folded back portion of the backsheet 14 in this embodiment) between the backsheet 14 and the inner sheets 18, and 18' by fixing means such as a hot melt, thereby forming a pair of leg gathers 24, and 24', respectively. The first elastically expansible members 22, and 22' are arranged on the disposable diaper 10 along its longitudinal direction and over an area from a lower end edge portion 52' of the back-side waist gathers 52 to a lower end edge portion 53' of the front waist gathers 53.

Second elastically expansible members 26, and 26' are fixedly arranged in their stretched states, as shown in FIGS. 1 and 2, on inner side edges of the inner sheets 18, 18', respectively, by fixing means such as a hot melt or the like, thereby forming a pair of frill portion gathers 28, and 28'. The second elastically expansible members 26, and 26' are arranged, as in the case with the first elastically expansible members 22, and 22', on the disposable diaper 10 along the longitudinal direction and over an area from the lower end edge portion 52' of the rear waist gathers 52 to a lower end edge portion 53' of the front waist gathers 53. As shown in FIG. 2, the second elastically expansible members 26, 26' are arranged on a folded back portion formed by folding back the inner side edges of the inner sheets 18, and 18' towards the topsheet 12 side.

As the material for the first and second elastically expansible members, the same material as used for the waist elastically expansible member may be used or it may be a different material. In other words, the material for the first and second elastically expansible members is not particularly limited.

In the disposable diaper according to this embodiment, the topsheet 12 and the inner sheets 18, and 18' are fixedly jointed by fixing means such as a hot melt or the like. As shown in FIG. 2, the fixedly jointing portions F, F are located within the longitudinal side edges 20, and 20' of the absorbent member 16 and the inner side edges of the inner sheets 18, 18' and along the longitudinal direction of the diaper. Accordingly, the areas on the inner sheets 18, and 18' from the frill portion gathers 28, and 28' formed on the inner side edges to the fixedly jointing portions F, F are not secured to the topsheet 12 and are in free states. As a consequence, in the disposable diaper 10, a pair of frill portions 30, and 30' are formed on the topsheet 12 side such that the frill portion gathers 28, and 28' define free edges. That is, the longitudinal side edge portions of the frill portions 30, and 30' are defined as free edges, and the frill portion gathers 28, and 28' are formed on the free edges. On the other hand, the side edge portions (which correspond to the fixedly jointing portions F,F) disposed opposite the above-mentioned free edges are fixedly jointed to the topsheet 12.

Furthermore, in the disposable diaper according to this embodiment, as shown in FIGS. 1 and 2, the approximate centers of the frill portion gathers 28, and 28' along the longitudinal direction and inner portions located inwardly from the approximate centers of the leg gathers 24, and 24 along the longitudinal direction thereof are fixedly jointed together at the fixedly jointing portions F', F' so that the frill portions 30, and 30' and the leg gathers 24, and 24' are raised. For fixedly jointing the frill portion gathers and the leg gathers, such fixing means as a hot melt or the like can be used. The fixedly jointing portions F', F' may be fixedly jointed with a degree of strength sufficient for the frill portion gathers and the leg gathers to be raised, and sufficient to maintain the raised states in use, and the fixedly jointing area (length, width) is not particularly limited. The leg gathers 24, and 24' are fixedly jointed to the frill portion gathers 28, 28' at inner portions located inwardly from the approximate centers of the leg gathers along the longitudinal direction of the leg gathers. The locations of the inner portions can properly be adjusted (that is, displaced either inwardly or outwardly) so that the frill portion gathers and the leg gathers are raised as originally intended.

In the disposable diaper according to this embodiment, as shown in FIG. 1, the longitudinal side portions of the rear waist body portion 50 of the diaper have fixing members 32, and 32' located on the topsheet side of the longitudinal side portions. These fixing members 32, and 32' are adapted so that the rear waist body portion 50 and the front waist body portion 51 of the diaper are fixed together, as shown in FIG. 3, when the disposable diaper according to the present invention is worn.

As the fixing members, those members which are used for the conventional disposable diapers can be used without any limitation. In this embodiment, as described above, it is preferred that as the fixing members, those which are known as mechanical fasteners (male side) are used, and as those members to be fixed, non-woven fabrics are used. More specifically, since an outer surface of the disposable diaper according to this embodiment on the backsheet side is composed of a non-woven fabric as the members to be fixed, the rear waist body portion 50 and the front waist body portion 51 are secured together by the non-woven fabric and the mechanical fasteners as the fixing members. As a result, the fixing members can be secured to any part of the members to be fixed. Accordingly, the size of the waist portion of the diaper can easily be adjusted in match with the body dimensions of the wearer. Moreover, since the fixing members and the members to be fixed are removably attached, when it is required to temporarily take off the diaper from the wearer in order to check the inside conditions of the diaper, it can easily be put on the wearer again. That is, the diaper can be put on and off as often as required.

Figure 4:
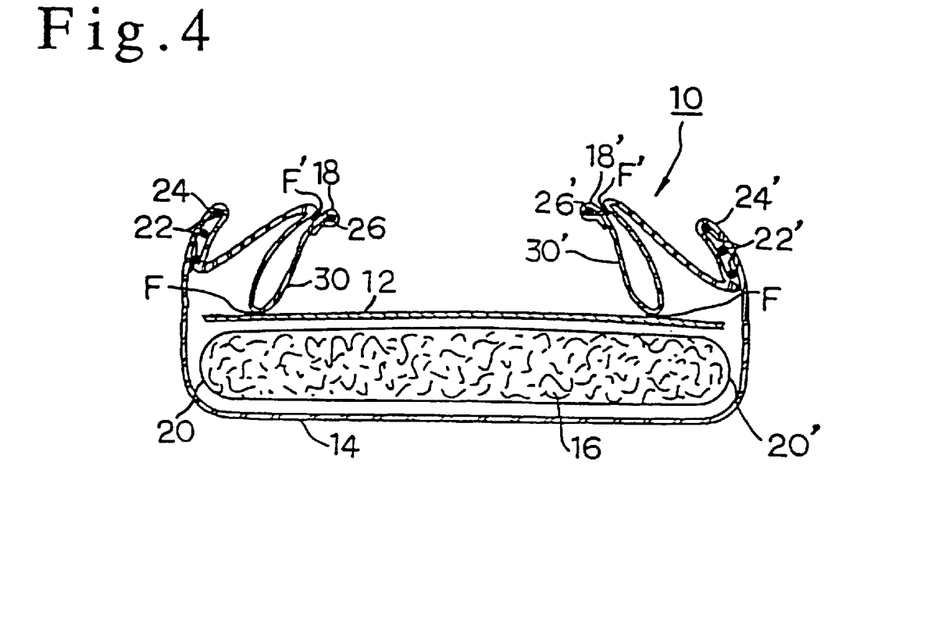
FIG. 4 is a view (corresponding to FIG. 2) showing the first embodiment of a disposable diaper according to the second aspect of the invention.
Figure 5:
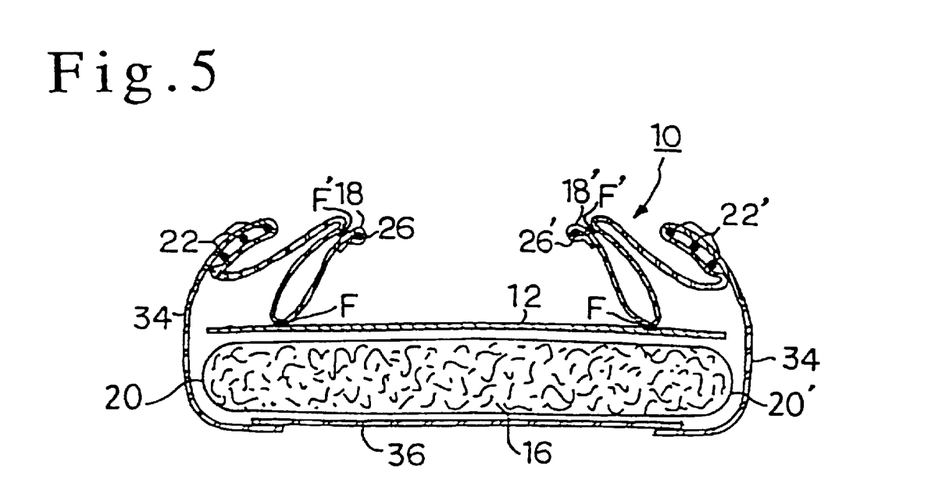
FIG. 5 is a view (corresponding to FIG. 2) showing the second embodiment of a disposable diaper according to the second aspect of the invention.

Next, preferred embodiments of the disposable diaper according to the second aspect of the invention will be described with reference to FIGS. 4 and 5. FIG. 4 is a view (corresponding to FIG. 2) showing a first embodiment of a disposable diaper according to the second aspect of the invention, and FIG. 5 is a view (corresponding to FIG. 2) showing a second embodiment of a disposable diaper according to the second aspect of the invention. In FIGS. 4 and 5, although the same points as in FIGS. 1 through 3 are not particularly described, the detailed description made with reference to FIGS. 1 through 3 is applicable, where appropriate. In FIGS. 4 and 5, identical members as in FIGS. 1 through 3 are denoted by identical reference numerals.

The disposable diaper 10 according to the first embodiment shown in FIG. 4 is constituted similarly to the disposable diaper of the first aspect of the invention, and the developed state thereof is similar to that shown in FIG. 1. The disposable diaper of the embodiment shown in FIG. 4 is different from the disposable diaper of the first embodiment in respect that each of the inner sheets 18, and 18' comprises a single sheet. The backsheet 14 also comprises a single sheet. Further, the inner sheets 18, and 18' are formed as a continuous member formed by folding the backsheet 14. As the sheet material constituting the inner sheet and the backsheet, the above-mentioned liquid impermeable sheet having moisture permeable properties is preferably used.

A disposable diaper according to the second embodiment as shown in FIG. 5 has generally the same construction as the disposable diaper according to the first embodiment and is different from the latter only in respect that the backsheet comprises a non-woven fabric 36, and both the longitudinal side portions thereof are connected to a film 34. The films 34, 34 are folded back towards the topsheet 12 side of the diaper to thereby form the inner sheets 18 and 18'. The film 34 and the non-woven fabric 36 may be connected together by fixing means such as hot melt, heat seal or the like. In the disposable diaper according to the second embodiment, since the fixing members can also be secured to any location of the non-woven fabric by commonly using the mechanical fasteners as fixing members as in the case with the disposable diaper according to the first aspect of the invention, the size of the waist portion of the diaper can be adjusted appropriately in match with the body dimensions of the wearer. Moreover, since the fixing members can be attached and detached as often as required, the diaper which is temporarily taken off from the wearer can easily be put on the wearer. In the disposable diaper according to the second embodiment, since the amount of use of the non-woven fabric 36 can be reduced, manufacturing cost can be lowered.

Figure 6:
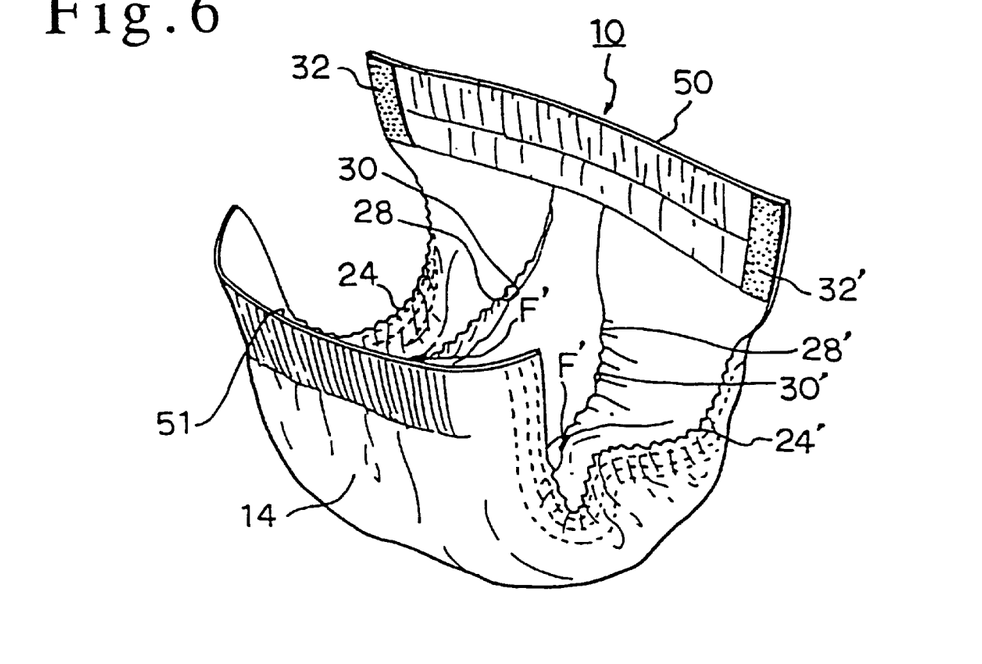
FIG. 6 is a perspective view showing a relaxed state of the disposable diaper according to the first embodiment of the second aspect of the invention.
Figure 7:
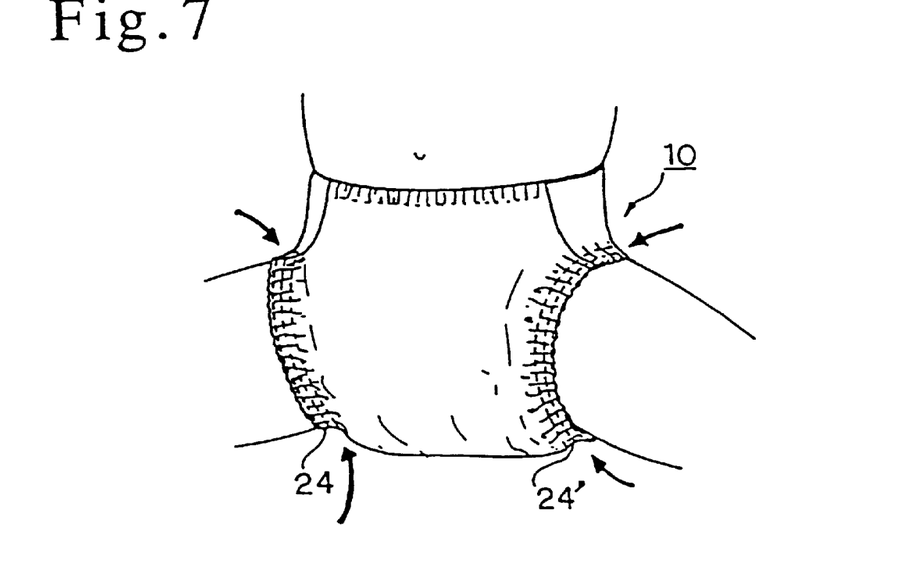
FIG. 7 is a view showing the state that the disposable diaper of the first embodiment of the second aspect of the invention is put on the diaper wearer.

Next, the liquid absorption function of the disposable diaper according to the second aspect of the invention will be described with reference to FIGS. 6 through 8. Here, FIG. 6 is a view showing the relaxed state of the disposable diaper according to the first embodiment of the second aspect of the invention, FIG. 7 is a view showing the state that the disposable diaper according to the first embodiment of the second aspect of the invention is put on the wearer, and FIG. 8 a view showing a cross section of the disposable diaper according to the first embodiment of the second aspect of the invention in its relaxed state, taken on line B—B in FIG. 1 which is a development view corresponding to the development view of the disposable diaper according to the first embodiment of the second aspect of the invention.

In the disposable diaper according to the second aspect of the invention, approximate center portions of the frill portion gathers 28, and 28' along the longitudinal direction thereof and inner portions located inwardly from the approximate centers of the leg gathers 24, and 24' along the longitudinal direction thereof are joined together such that the frill portions 30, and 30' and the leg gathers 24, and 24' are raised. The frill portions and leg gathers are in their raised states when the disposable diaper according to the second aspect of the invention is developed (see FIG. 4). Moreover, in the relaxed state of the disposable diaper according to the second aspect of the invention as shown in FIG. 6, the frill portions and the leg gathers are more sharply raised. Accordingly, not only the frill portions but also the leg gathers take the three-dimensional configurations unlike conventional disposable diapers, and in addition, these members are formed into a unitary body. Accordingly, leakage of liquid from the areas around the wearer's legs can more effectively be prevented than in conventional disposable diapers. Moreover, the frill portions and the leg gathers are rounded when the diaper is in use. In addition, as shown in FIG. 7, the leg gathers 24, and 24' are in contact at their surfaces with the wearer's legs (as indicated by arrows of FIG. 7). Accordingly, the diaper exhibits markedly enhanced fittingness, and leakage of liquid can more effectively be prevented.

Figure 8:
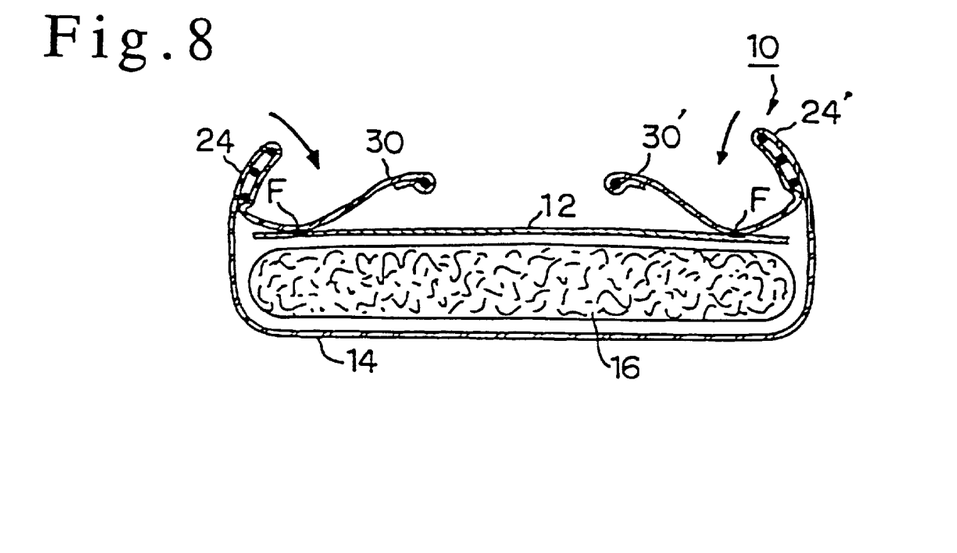
FIG. 8 is a view showing a cross section of the disposable diaper according to the first embodiment of the second aspect of the invention in its relaxed state, taken on line 8—8 in FIG. 1 which is a development view corresponding to the development view of the disposable diaper according to the first embodiment of the second aspect of the invention.

As shown in FIG. 8, since a so-called pocket portion for receiving discharged materials is formed (as indicated by arrows of FIG. 8) by the frill portions 30, and 30', receivability of discharged material is remarkably increased. This pocket portion is particularly effective for preventing liquid from leaking from the waist body portion.

As shown in FIG. 8, in the disposable diaper according to the second aspect of the invention, leakage of liquid, even if would occur over the frill portions 30, and 30', due to wearer's motion or the like any liquid will be absorbed by the absorbent member 16 located between the frill portions and the leg gathers and will not leak outside the diaper. Accordingly, the leakage of liquid is more effectively prevented. In order to more effectively absorb the leakage of liquid between the frill portions and the leg gathers, the outer surface (i.e., the surface facing the leg gathers when the frill portions are raised) of the frill portions are preferred to have hydrophilic properties. In order that those areas have such hydrophilic properties, for example, the frill portions may be made of material having hydrophilic properties or the frill portions may be subjected to hydrophilic treatment using a surface active agent or the like.

Figure 9:
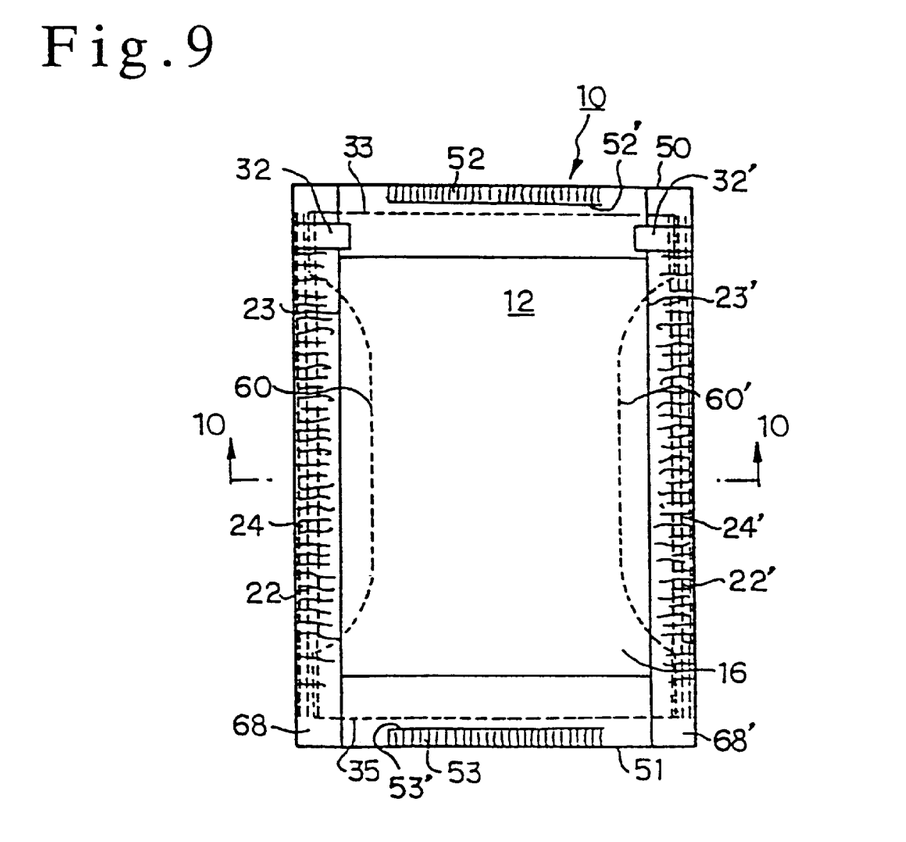
FIG. 9 is a development view of a disposable diaper of this embodiment.
Figure 10:
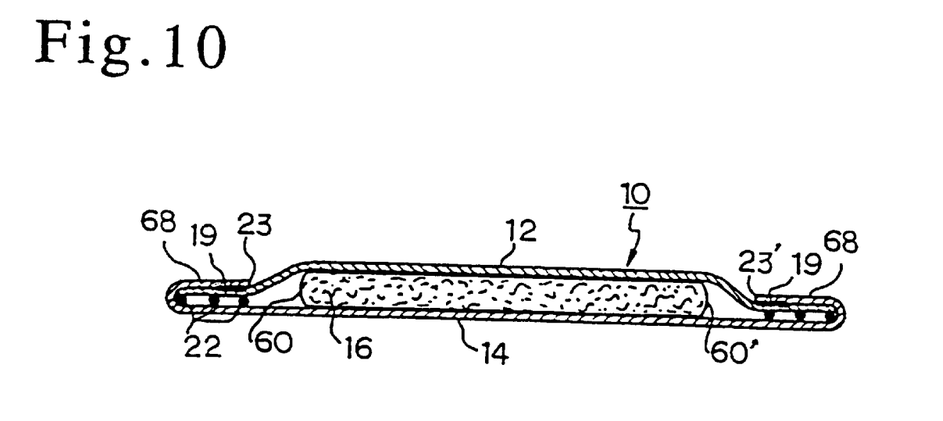
FIG. 10 is a sectional view taken on line 10—10 of the disposable diaper of FIG. 9.

Next, another embodiment of the invention will be described with reference to FIGS. 9 and 10. FIG. 9 is a development view of a disposable diaper of this embodiment, and FIG. 10 is a sectional view taken on line 10—10 of the disposable diaper of FIG. 9. Although the same points in this embodiment as those in the first and second aspect of the invention are not particularly described, the detailed descriptions made with respect to the first and second aspect of the invention are applicable, where appropriate. In FIGS. 9 and 10, identical members as in FIGS. 1 through 8 are denoted by identical reference numerals.

In the disposable diaper according to this embodiment, as shown in FIG. 9 and 10, folded-back sheets 68, and 68' which are connected with the backsheet 14 are provided on opposite longitudinal side portions of the disposable diaper 10 on its topsheet 12 side. An area on the topsheet 12 side other than the folded-back sheets 68, and 68' serves as a liquid absorbing area.

More specifically, in the disposable diaper according to this embodiment, as shown in FIGS. 9 and 10, opposite longitudinal side portions of the backsheet 14 are folded back towards the topsheet 12 side, thereby forming folded-back sheets 68, and 68' which are connected with the backsheet 14. The sheets 68, and 68' are disposed over an entire longitudinal length of the disposable diaper 10. The widths of the sheets 68, and 68' are approximately the same. In view of liquid absorption through the entire surface, the total width of the folded-back sheets 68, and 68' is preferably 10 to 50% of the width of the disposable diaper when viewing the topsheet side of the flattened state diaper (as shown in FIG. 9) from the direction perpendicular to the topsheet.

As shown in FIGS. 9 and 10, the longitudinal inner side edges 23, and 23' of the sheets 68, 68' are located outwardly of the widthwise narrowest portions 60, 60' (most significantly twisted portions) of the absorbent member 16.

The sheets 68, and 68' in the disposable diaper according to this embodiment as shown in FIGS. 9 and 10 are formed as a continuous member obtained by folding back the backsheet 14. Accordingly, the material of the sheets 68, and 68' is the same as that of the backsheet 14. However, the material of the sheets in the disposable diaper according to this embodiment may be different from that of the backsheet as in the embodiments of FIGS. 15 and 16 as later described.

In the disposable diaper of this embodiment, as shown in FIGS. 9 and 10, opposite side edge portions thereof, i.e., folded-back portions of the backsheet 14, are provided with elastically expansible members 22, and 22', which are secured thereto in expanded states by fixing means such as a hot melt or the like, thereby forming a pair of leg gathers 24, and 24'. As a consequence, when the expansible members are relaxed, the leg gathers 24 and 24' are raised towards the side of the topsheet owing to the leg gathers 24, and 24'. The elastically expansible members 22, and 22' are arranged from the upper end edge portion 33 to the lower end edge portion 35 of the absorbent member 16 along the longitudinal direction of the disposable diaper 10. In this case, a plurality of elastically expansible members are preferably provided at least at opposite side edge portions of the diaper to form the leg gathers. The degrees of elongation of the elastically expansible members preferably become greater as the plurality of elastically expansible members go outwardly of the diaper, so that the leg gathers have rounded-shapes, respectively. For example, in this embodiment, as shown in FIGS. 9 and 10, three elastically expansible members which make up each of 22, and 22' are provided on opposite side edge portions of the diaper. The degree of elongation of the elastically expansible member which is located most outwardly, and the degrees of elongation of the two elastically expansible members which are located inwardly are gradually reduced. By adjusting the degrees of elongation of the elastically expansible members in this way, the leg gathers 24, 24' can be formed into the preferable rounded shapes.

As shown in FIG. 10, in the disposable diaper of this embodiment, opposite inner portions of the sheets 68, and 68' are fixedly jointed to the topsheet 12 by fixing means 19, and 19' such as hot melt or the like.

Figure 11:
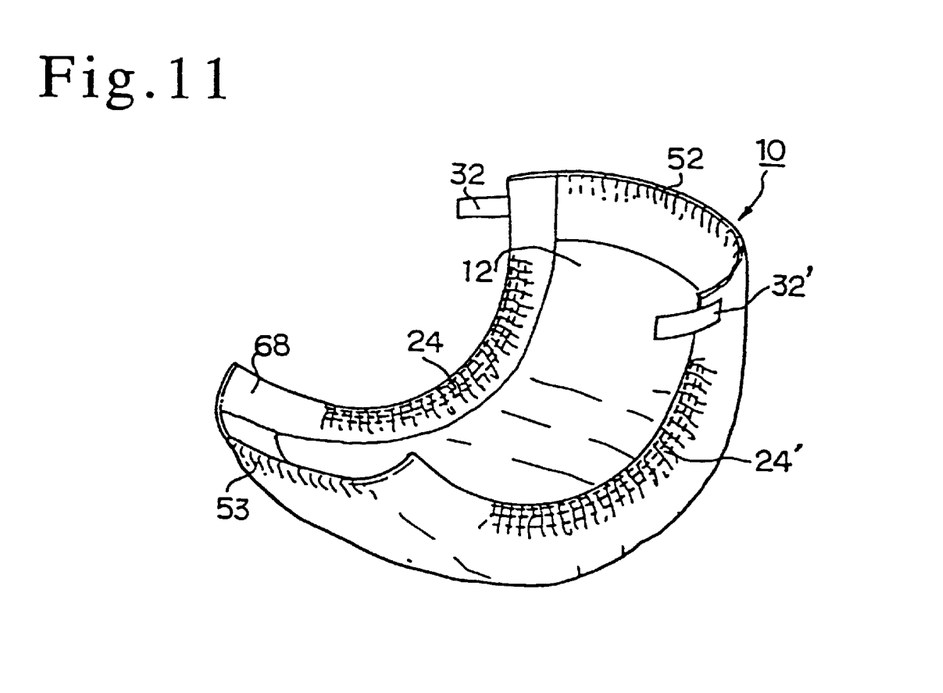
FIG. 11 is a perspective view showing a relaxed state of the disposable diaper of FIG. 9.

In the disposable diaper according to this embodiment, as shown in FIG. 11, the opposite side portions of the diaper are raised toward the topsheet side when the disposable diaper according to the present invention is brought to its relaxed state, i.e., to its developed state for use, owing to the leg gathers 24, and 24'. Moreover, the opposite side portions are in rounded shapes which match the areas around the wearer's legs due to the leg gathers 24, and 24'. As a consequence, when such a disposable diaper is put on, the leg gathers 24, 24' are in contact at their surfaces with the wearer's legs. Accordingly, the diaper exhibits markedly enhanced fittingness, and leakage of liquid can more effectively be prevented. Moreover, since the parts of the leg gathers 24, and 24', which are in contact with the areas around the wearer's legs, are formed of the liquid impermeable (i.e., hydrophobic) sheets 68, and 68', leakage of liquid from the leg gathers can more effectively be prevented.

As described above, in the disposable diaper according to this embodiment, owing to the feature that other portion than the sheets 68, 68' on the side of the topsheet 12 serves as a liquid absorbing area, a wider liquid absorbing area can be obtained. Moreover, since the discharged material can be prevented from locally absorbed, the inherent absorbing performance of the absorbent member can fully be exhibited.

Figure 12:
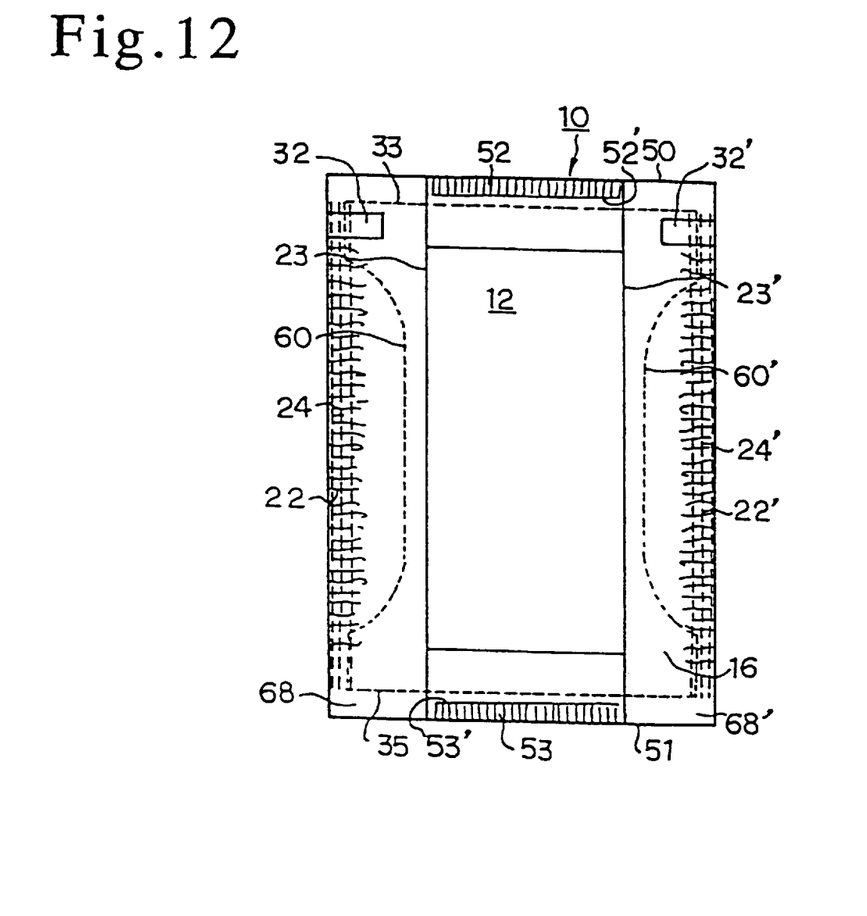
FIG. 12 is a development view (corresponding to FIG. 9) showing another embodiment of the disposal diaper of FIG. 9.
Figure 13:
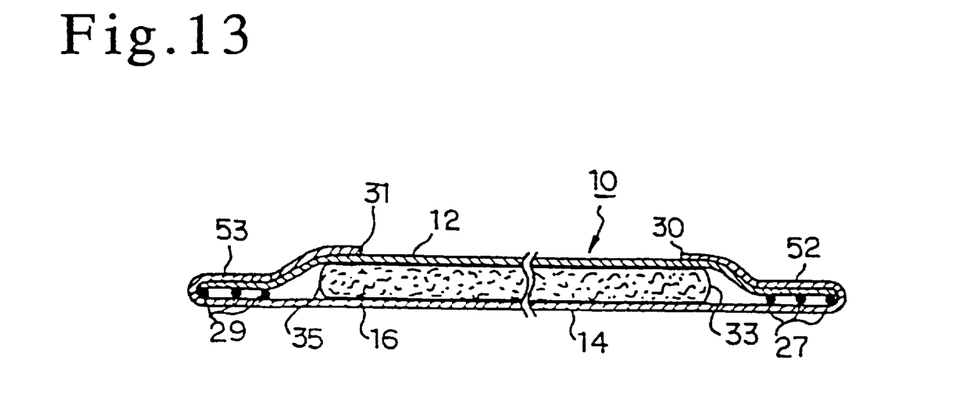
FIG. 13 is a sectional view of the disposable diaper according to another embodiment of FIG. 9 taken on the longitudinal center line.
Figure 14:
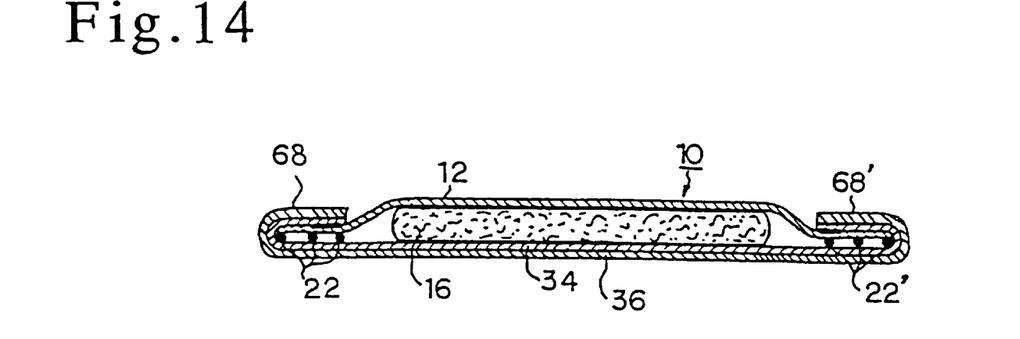
FIG. 14 is a sectional view (corresponding to FIG. 10) showing a widthwise cross section of another embodiment of the disposable diaper according to FIG. 9.
Figure 15:
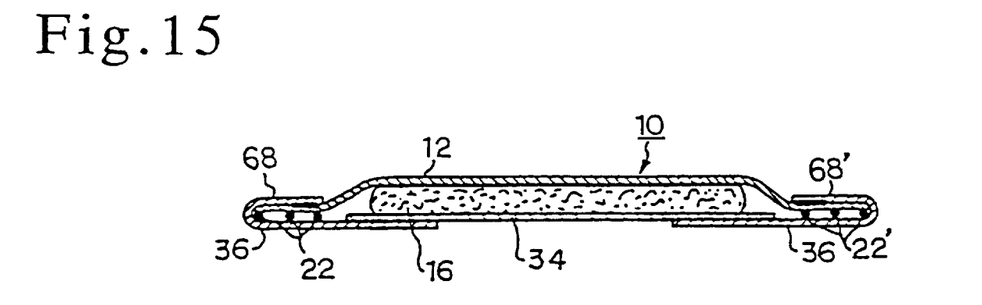
FIG. 15 is a sectional view (corresponding to FIG. 10) still showing a widthwise cross section of another embodiment of the disposable diaper according to FIG. 9.
Figure 16:
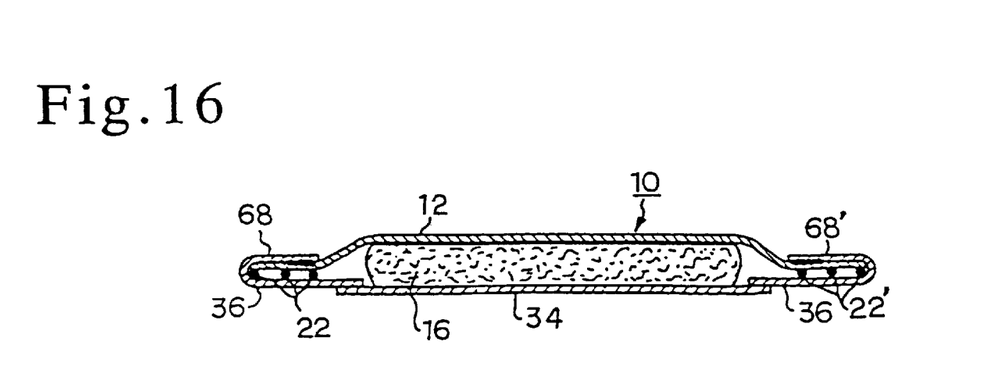
FIG. 16 is a sectional view (corresponding to FIG. 10) still showing a widthwise cross section of another embodiment of the disposable diaper according to FIG. 9.
Figure 17:
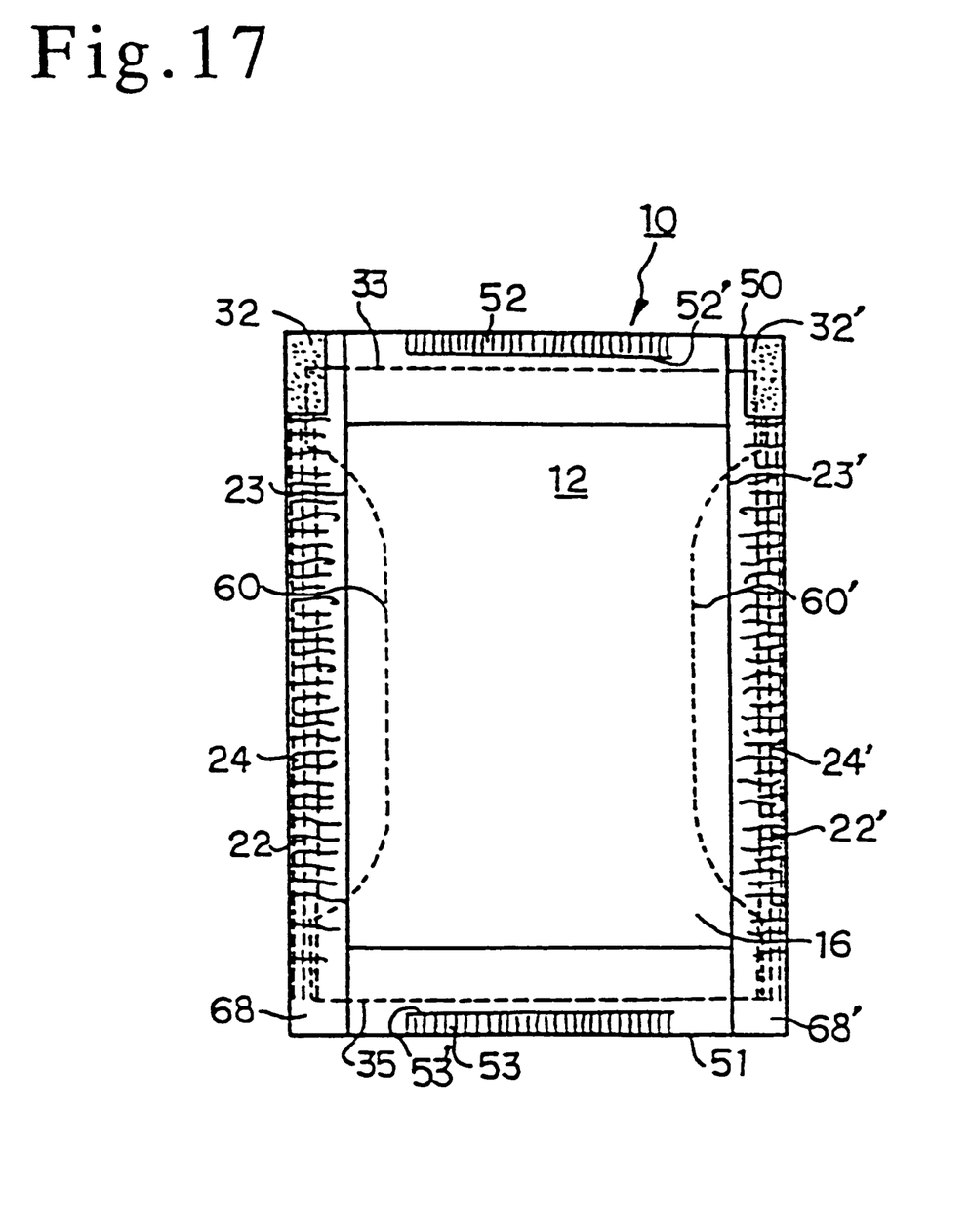
FIG. 17 is a development view (corresponding to FIG. 9) still showing another embodiment of the disposable diaper according to FIG. 9.

Next, additional embodiments of the disposable diaper according to the embodiment of FIG. 9 will now be described with reference to FIGS. 12 through 17. FIG. 12 is a development view (corresponding to FIG. 9) showing another embodiment of the disposable diaper of FIG. 9; FIG. 13 is a sectional view of the disposable diaper according to another embodiment of FIG. 9 taken on the longitudinal center line; FIG. 14 is a sectional view showing a widthwise cross section of another embodiment of the disposable diaper according to FIG. 9; FIG. 15 is a sectional view still showing a widthwise cross section of another embodiment of the disposable diaper according to FIG. 9; FIG. 16 is a sectional view still showing a widthwise cross section of another embodiment of the disposable diaper according to FIG. 9; and FIG. 17 is a development view still showing another embodiment of the disposable diaper according to FIG. 9.

In these embodiments, although the same points as in the embodiment of FIG. 9 are not particularly described, the detailed description made with reference to the embodiment of FIG. 9 is applicable, where appropriate. In FIGS. 12 through 17, identical members as in FIGS. 9 through 11 are denoted by identical reference numerals.

A disposable diaper according to the embodiment of FIG. 12 is constructed generally in the same manner as in the embodiment of FIG. 9, except that the longitudinal inner side edges 23, and 23' of the sheets 68, and 68' are located inwardly of the widthwise narrowest portions 60, and 60' of the absorbent member 16. In this case, in the sheets 68, 68', at least opposite outer portions thereof are fixedly jointed to the topsheet 12 by fixing means (not shown) such as a hot melt or the like. In a disposable diaper thus constructed, since the longitudinal opposite side portions of the absorbent member 16 are covered with the folded-back sheets 68, and 68' having liquid impermeable properties (i.e., hydrophobic properties), body fluids absorbed are prevented from returning to the wearer's skin side even when a body pressure or the like is applied to the areas around the wearer's legs.

A disposable diaper according to the embodiment of FIG. 13 is constructed generally in the same manner as the disposable diaper of FIG. 9, except that longitudinal upper and lower end portions of the backsheet 14 are folded back towards the side of the topsheet 12, and the folded-back portions are provided respectively with waist elastically expansible members 27, 29, so that rear waist gathers 52 and front waist gathers 53 are formed in the width direction of the diaper. In this case, the upper and lower end edge portions 30, 31 are folded back such that they go beyond the upper and lower end edge portions 33, 35 of the absorbent member 16 and exist on the absorbent member 16. The folded-back widths of the backsheet 14 on the side of the rear waist gathers 52 and on the side of the front waist gathers 53 are almost the same. In a disposable diaper thus constructed, since the upper and lower end portions of the absorbent member 16 are covered with the backsheet 14 having liquid impermeable properties (i.e., hydrophobic properties), body fluids once absorbed are prevented from returning to the wearer's skin side even when a body pressure or the like is applied to the wearer's waist portion.

A disposable diaper according to the embodiment of FIG. 14 has generally the same construction as the disposable diaper according to FIG. 9. The disposable diaper of FIG. 14 is different from the disposable diaper of FIG. 9 in respect that the backsheet 14 and the sheets 68, and 68' are formed into a unitary body and each comprise a laminate of a non-woven fabric 36 and a liquid impermeable film 34, and are arranged such that the non-woven fabric is located on the side of the absorbent member of the diaper. As a result, similar advantageous effects to those produced by the disposable diaper of the first aspect of the invention can be obtained.

A disposable diaper according to the embodiment of FIG. 15 has generally the same construction as the disposable diaper according to FIG. 9 and is different from the latter only in the respect that the backsheet comprises a film 34 and the non-woven fabrics 36, 36 disposed on the longitudinal opposite side portions are connected with each other in such a manner as to cover the film 34. The non-woven fabric 36 is folded back towards the topsheet 12 side of the diaper to thereby form the folded-back sheets 68, 68'. The film 34 and the non-woven fabric 36 may be connected together by fixing means such as hot melt, heat seal or the like. The disposable diaper according to this embodiment is effective when an adhesive tape such as a fastening tape is used as the fixing members (securing members) and the adhesive tape is attached to the film end portion. In the disposable diaper according to the embodiment of FIG. 15, since the amount of use of the non-woven fabric 36 can be reduced compared with the disposable diaper of the embodiment of FIG. 14, manufacturing cost can be lowered.

A disposable diaper according to FIG. 16 is constructed generally in the same manner as the disposable diapers according to the FIG. 9 and FIG. 15 embodiments, except that the backsheet comprises a film 34, and the non-woven fabrics 36, 36 are continuously arranged on longitudinal opposite side portions at an inner surface (i.e., surface contacting the absorbent member 16) of the film 34. The non-woven fabrics 36 are folded back towards the topsheet 12 side to thereby form the folded-back sheets 68, 68'. The film 34 and the non-woven fabric 36 may be connected together by fixing means such as hot melt, heat seal or the like as in the FIG. 15 embodiment. The disposable diaper according to this embodiment is also effective as in the diaper of FIG. 15 when an adhesive tape such as a fastening tape is used as the fixing members (securing members) and the adhesive tape is attached to the film end portion. In the disposable diaper according to the FIG. 16 embodiment, since the amount of use of the non-woven fabric 36 can be much more reduced compared with the disposable diapers of the FIGS. 14 and 15 embodiments, manufacturing cost can be much more lowered.

A disposable diaper according to the embodiment of FIG. 17 is constructed in the same manner as in the FIG. 9 embodiment, except that opposite side portions on the topsheet 12 side of the waist portion 50 on the backsheet side are provided directly with mechanical fasteners 32, 32' as a fixing member. Use of such fixing members can also achieve the same effect as the disposable diaper according to the FIG. 9 embodiment.

Although the disposable diaper according to the present invention is described hereinbefore with reference to preferred embodiments, it should be noted that the disposable diaper according to the present invention are not limited to the above embodiments and many modifications can be made. For example, a liquid impermeable sheet may be interposed between the topsheet and the absorbent member in the rear waist body portion and/or the front waist body portion so that a so-called waist barrier is formed in order to prevent the liquid from oozing when the diaper wearer is laid in a horizontal posture. The inner sheets or the folded-back sheets are not necessarily arranged over the entire longitudinal length of the diaper but they may be arranged only at an area from a lower end edge portion 52' of the rear waist gathers 52 to a lower end edge portion 53' of the front waist gathers 53. As the fixing member, a mechanical fastener and an adhesive tape such as a fastening tape can be replaceably used in an appropriate manner according to necessity.

INDUSTRIAL APPLICABILITY

As described hereinbefore in detail, according to the first aspect of the invention, the backsheet comprises a laminate of the liquid impermeable film and the non-woven fabric, and the backsheet is arranged such that the non-woven fabric is located on an outer surface of the diaper. Accordingly, there can be obtained a disposable diaper having the feel something like a cloth and able to offer a pleasant feel of use. Further, by commonly using the mechanical fasteners as the fixing members, the fixing members can be secured to any part of the non-woven fabric. Accordingly, the size around the wearer's body can appropriately be adjusted in match with the physical bodily structure of the wearer.

According to the second aspect of the invention, there is provided a disposable diaper, in which liquid can assuredly be absorbed and prevented from leaking when the liquid tends to disperse in various directions in accordance with motion of the diaper wearer.

According to the alternative embodiment of the invention, there is provided a disposable diaper, in which liquid can assuredly be absorbed through the entire surface of the diaper by prohibiting local absorption, inherent absorbing performance of an absorbent member can fully be exhibited by preventing local absorption of discharged material, and such unfavorable occurrences as slip-down, leakage, bagginess and the like do not happen even if the weight of discharged material is applied to the diaper.

We claim:

1. A disposable diaper comprising a liquid permeable topsheet, a liquid impermeable backsheet, and a liquid retentive absorbent member interposed between the topsheet and the backsheet, said absorbent member including first and second substantially planar sides, said topsheet being positioned on said first substantially planar side, and having a pair of inner sheets which include continuous extensions of the backsheet and are provided at opposite longitudinal side portions of the disposable diaper on its topsheet side and on said first substantially planar side of said absorbent member such that longitudinal inner side edges of the inner sheets are positioned inwardly with respect to the longitudinal side edges of the absorbent member;

first elastically expansible members provided within first folded portions of said backsheet which are located between portions of the backsheet positioned on said second side of said absorbent member and each of the inner sheets to form leg gathers, and second elastically expansible members provided within second folded portions of said backsheet which include the inner side edges of each of the inner sheets, said second folded portions and said second expansible members form frill portion gathers;

the topsheet and the inner sheets being attached together with respect to a region located within the longitudinal side edges of the absorbent member on said first substantially planar side of said absorbent member and the inner side edges of the inner sheets such that the frill portion gathers define free edges spaced from said topsheet, and approximate center portions of the frill portion gathers along the longitudinal direction thereof and inner portions located inwardly from the approximate centers of the leg gathers along the longitudinal direction thereof are connected together such that the frill portions and leg gathers are spaced from said topsheet, whereby said frill portions provide three-dimensional gathers which substantially reduce leakage of bodily secretions from the diaper.

2. The disposable diaper according to claim 1, wherein the backsheet comprises a laminate of a non-woven fabric and a film, and is arranged such that the non-woven fabric is located on the outer skin-noncontacting surface side of the laminate.

3. The disposable diaper according to claim 1, wherein each of the inner sheets comprises a laminate of a non-woven fabric and a film, and is arranged such that the non-woven fabric is located on the side of the skin-contacting surface of the diaper.

4. The disposable diaper according to claim 1, wherein each of longitudinal side portions of a rear waist body portion of the diaper has on its topsheet side a fixing member for fixing the rear waist body portion and a front waist body portion of the diaper when the diaper is worn.

5. The disposable diaper according to claim 4, wherein each of the fixing members comprises a mechanical fastener provided on a surface of a support member.

6. The disposable diaper according to claim 1, wherein the total width of the inner sheets provided at opposite longitudinal side portions of the disposable diaper is 55% or more of the width of the disposable diaper.

7. The disposable diaper of claim 1, wherein said backsheet includes portions which extend substantially perpendicularly with respect to the topsheet side of the diaper.

8. The disposable diaper of claim 1, further comprising first and second waist portions, each waist portion including gathers.

9. A disposable diaper comprising a liquid permeable topsheet, a liquid impermeable backsheet, and a liquid retentive absorbent member interposed between the topsheet and the backsheet, said absorbent member including first and second substantially planar sides, said topsheet being positioned on said first substantially planar side, and having a pair of inner sheets which include continuous extensions of the backsheet and are provided at opposite longitudinal side portions of the disposable diaper on its topsheet side and on said first substantially planar side of said absorbent member such that longitudinal inner side edges of the inner sheets are positioned inwardly with respect to the longitudinal side edges of the absorbent member;

first elastically expansible members provided at first portions of said backsheet which are located adjacent to said second side of said absorbent member and adjacent to a respective inner sheet to form leg gathers, and second elastically expansible members provided at second portions of said backsheet which include the inner side edges of each of the inner sheets, said second expansible members form frill portion gathers;

the topsheet and the inner sheets being attached together with respect to a region located within the longitudinal side edges of the absorbent member on said first substantially planar side of said absorbent member and within the longitudinal inner side edges of the inner sheets such that the frill portion gathers define free edges spaced from said topsheet, and a portion of said frill portion gathers is attached to a portion of said inner sheet located between said frill portion gathers and said leg gathers, whereby said frill portion gathers provide three-dimensional gathers which substantially reduce leakage of bodily secretions from the diaper.

10. The disposable diaper of claim 9, wherein said backsheet includes portions which extend substantially perpendicularly with respect to the topsheet side of the diaper.

11. The disposable diaper of claim 9, further comprising first and second waist portions, each waist portion including gathers.

12. A disposable diaper comprising a liquid permeable topsheet, a liquid impermeable backsheet, and a liquid retentive absorbent member interposed between the topsheet and the backsheet, said absorbent member including first and second substantially planar sides, said topsheet being positioned on said first substantially planar side, and having a pair of inner sheets which include continuous extensions of the backsheet and are provided at opposite longitudinal side portions of the disposable diaper on its topsheet side and on said first substantially planar side of said absorbent member such that longitudinal inner side edges of the inner sheets are positioned inwardly with respect to the longitudinal side edges of the absorbent member;

first elastically expansible members provided at first portions of said backsheet which are located adjacent to said second side of said absorbent member and adjacent to a respective inner sheet to form leg gathers, and second elastically expansible members provided at second portions of said backsheet which include the inner side edges of each of the inner sheets, said second expansible members form frill portion gathers;

the topsheet and the inner sheets being attached together with respect to a region located within the longitudinal side edges of the absorbent member on said first substantially planar side of said absorbent member and within the longitudinal inner side edges of the inner sheets such that the frill portion gathers define free edges spaced from said topsheet, and a portion of said inner sheets located between the leg gathers and said attachment between the topsheet and the inner sheets being free from attachment with said topsheet, whereby said frill portion gathers provide three-dimensional gathers which substantially reduce leakage of bodily secretions from the diaper.

* * * * *